C12) United States Patent
Thoms

US007014925B2

(10) Patent No.: US 7,014,925 B2
(45) Date of Patent: Mar. 21, 2006

(54) HETEROGENEOUS SPIRO COMPOUNDS IN ORGANIC LIGHT EMITTING DEVICE ELEMENTS

(75) Inventor: Travis P. S. Thoms, San Lorenzo, CA (US)

(73) Assignee: Canon Kabushiki Kaisha, Tokyo (JP)

( * ) Notice: Subject to any disclaimer, the term of this patent is extended or adjusted under 35 U.S.C. 154(b) by 76 days.

(21) Appl. No.: 10/424,743

(22) Filed: Apr. 29, 2003

(65) Prior Publication Data

US 2004/0219386 A1    Nov. 4, 2004

(51) Int. Cl.
- H05B 33/12 (2006.01)
- C09K 11/06 (2006.01)
- C07D 311/96 (2006.01)
- C07F 7/08 (2006.01)

(52) U.S. Cl. ............... 428/690; 428/917; 252/301.16; 313/504; 313/506; 546/18; 549/331; 556/406

(58) Field of Classification Search ............... 428/690, 428/917; 558/46; 313/504, 506; 252/301.16; 257/40; 546/17, 18
See application file for complete search history.

(56) References Cited

U.S. PATENT DOCUMENTS

| 3,048,595 | A |   | 8/1962  | Zirkle ................. 546/17 |
| 3,721,672 | A |   | 3/1973  | Muller-Calgan et al. .... 544/230 |
| 4,001,418 | A |   | 1/1977  | Galt et al. ............ 546/17 |
| 4,001,419 | A |   | 1/1977  | Galt et al. ............ 546/17 |
| 4,198,420 | A |   | 4/1980  | Ong et al. ............ 514/278 |
| 4,268,514 | A |   | 5/1981  | Galt et al. ............ 514/278 |
| 4,503,066 | A |   | 3/1985  | Brittain et al. ........ 514/278 |
| 5,026,894 | A |   | 6/1991  | Tour et al. ............ 558/46 |
| 5,545,834 | A |   | 8/1996  | Singh et al. .............. 544/6 |
| 5,567,624 | A |   | 10/1996 | Smith ................ 436/163 |
| 5,621,131 | A |   | 4/1997  | Kreuder et al. ......... 558/46 |
| 5,698,740 | A |   | 12/1997 | Enokida et al. ........ 564/308 |
| 5,763,636 | A | * | 6/1998  | Kreuder et al. ......... 558/46 |
| 5,840,217 | A |   | 11/1998 | Lupo et al. ............ 252/583 |
| 5,859,211 | A |   | 1/1999  | Kreuder et al. ........ 528/403 |
| 5,900,327 | A |   | 5/1999  | Pei et al. ............. 428/690 |
| 5,936,070 | A |   | 8/1999  | Singh et al. .......... 530/591.3 |
| 5,942,340 | A |   | 8/1999  | Hu et al. ............. 428/690 |
| 5,989,737 | A |   | 11/1999 | Xie et al. ............ 428/690 |
| 6,002,000 | A |   | 12/1999 | Singh et al. ............. 544/6 |
| 6,004,685 | A |   | 12/1999 | Antoniadis et al. ...... 428/690 |
| 6,017,644 | A |   | 1/2000  | Toshida et al. ......... 428/690 |
| 6,132,641 | A |   | 10/2000 | Rietz et al. .......... 252/301.16 |
| 6,211,369 | B1 |   | 4/2001 | Salbeck et al. .......... 546/18 |
| 6,280,859 | B1 |   | 8/2001 | Onikubo et al. ......... 428/690 |
| 6,329,082 | B1 |   | 12/2001 | Kreuder et al. ........ 428/690 |
| 6,329,084 | B1 |   | 12/2001 | Tamano et al. ......... 428/690 |
| 6,337,404 | B1 |   | 1/2002 | Han et al. ............ 548/440 |
| 6,342,637 | B1 |   | 1/2002 | Han et al. ............ 564/434 |
| 6,361,884 | B1 |   | 3/2002 | Kreuder et al. ........ 428/690 |
| 6,376,694 | B1 |   | 4/2002 | Uchida et al. ......... 556/406 |
| 6,387,544 | B1 |   | 5/2002 | Thompson et al. ....... 428/690 |
| 6,458,476 | B1 |   | 10/2002 | Suzuki et al. ......... 428/690 |
| 2001/0023029 | A1 |   | 9/2001 | Shi et al. |
| 2001/0026878 | A1 |   | 10/2001 | Woo et al. |
| 2001/0046612 | A1 |   | 11/2001 | Lee et al. |
| 2002/0013451 | A1 |   | 1/2002 | Huang et al. |
| 2002/0033910 | A1 |   | 3/2002 | Ohnishi et al. |
| 2002/0045061 | A1 |   | 4/2002 | Hosokawa |
| 2002/0045062 | A1 |   | 4/2002 | Senoo et al. |
| 2002/0055013 | A1 |   | 5/2002 | Kim et al. |
| 2002/0057050 | A1 |   | 5/2002 | Shi |
| 2002/0061419 | A1 |   | 5/2002 | Woo et al. |
| 2002/0071963 | A1 |   | 6/2002 | Fujii |
| 2002/0081456 | A1 |   | 6/2002 | Hamada |

FOREIGN PATENT DOCUMENTS

| JP | 05-202355  |   | 8/1993 |
| JP | 581115     |   | 2/2002 |
| JP | 2003-096072 | * | 3/2003 |

OTHER PUBLICATIONS

Tour, t al., Jrnl. Org. Chem., vol. 61, No. 20, (Oct. 4, 1996).

* cited by examiner

Primary Examiner—Rena Dye
Assistant Examiner—Carnie S. Thompson
(74) Attorney, Agent, or Firm—Fitzpatrick, Cella, Harper & Scinto

(57) ABSTRACT

A family of non-polymeric heterogeneous spiro compounds having visible light emissive, hole-transport, electron transport or bipolar-transport properties may be used in organic light emitting devices (OLEDs), as an emissive layer in the OLEDs and/or in one or more of the charge transport layers, or as a host material for one or more of such layers.

9 Claims, No Drawings

HETEROGENEOUS SPIRO COMPOUNDS IN ORGANIC LIGHT EMITTING DEVICE ELEMENTS

BACKGROUND OF THE INVENTION

1. Field of the Invention

The present invention relates to a family of heterogeneous spiro compounds and to elements for organic light emitting devices (OLEDs) in which a heterogeneous spiro compound is used in the emissive layer and/or one or more of the charge transport layers, or as a host material for one or more of such layers.

2. Description of the Related Art

Organic light emitting devices (OLEDs) typically comprise a layer of emissive material between an anode and a cathode. When a bias is applied across the electrodes, positive charges (holes) and negative charges (electrons) are respectively injected from the anode and cathode into the emissive layer. The holes and the electrons form excitons in the emissive layer to emit light.

Electrodes are chosen to facilitate charge injection. A transparent indium-tin-oxide (ITO) anode has a relatively high work function and is therefore suitable for use as a hole injection electrode, while low work function metals such as Al, Mg and Ca are suitable for injection of electrons and are therefore a typical choice for the cathode.

To improve the power efficiency of an OLED, it is frequently desirable to enhance charge injection at the electrode interface. Hole transport layers and electron transport layers may be added adjacent the respective electrodes to facilitate charge transfer. Depending upon whether hole transport or electron transport is favored, the light emissive layer may be located closer to the anode or the cathode. In some instances, the emissive layer is located within the hole transport or electron transport layer.

Improved performance can be obtained if blocking layers are provided to block against the injection of either holes or electrons from the adjoining layer and their subsequent escape from the device. Likewise, a modifying layer may be used to improve the contact with one or both of the electrodes, or to improve the interface between two other layers.

Some of these layers can be combined. For example, a double-layered structure is fabricated from a combined hole-injecting and transporting layer together with a combined electron-transporting and light-emitting layer. Likewise, a triple-layered structure is composed of a hole-injecting and transporting layer, a light-emitting layer, and an electron-injecting and transporting layer.

Hole transport layers may include triarylamine-based materials, although many other hole transport materials are known. Likewise, an aluminum quinolinolate complex known as AlQ3 is a well known electron-transport material which has been used in OLEDs, although other electron transport materials are known.

Emissive materials having widely varied structures are known in the art and are generally selected based on color, brightness, efficiency and lifetime. These emissive materials may themselves also have electron transport or hole transport characteristics.

In addition, it is possible to form these layers from a "host" material doped with another material (the "guest" material) designed to achieve the desired effect of the layer (for example, to achieve a hole transport effect, an electron transport effect, or an emissive effect). In the case of an emissive guest-host system, the host must be able to transfer energy to the guest so that a maximum amount of energy contributes to emission by the guest rather than being absorbed by the host.

Anthracene and fluorene both have emissive characteristics, and OLED materials based on these compounds have been described in the literature. Spiro compounds comprising an acridine moiety (acridine has the structure of anthracene except that the 10 position is occupied by a nitrogen atom) are also known to have chemiluminescent properties. Likewise, certain xanthene-based compounds have been shown to have luminescent properties (xanthene has the structure of anthracene except that the 10 position is occupied by an oxygen atom.) Spiro bis-fluorene compounds have been disclosed for use in OLEDs. However, there continues to be a need in the art for spiro compounds in which heterogeneous groups are bridged via the spiro atom to impart novel energy transfer, charge transfer and/or emissive properties to the compound overall. It would likewise be desirable to develop "small" (i.e. non-polymeric) compounds having the aforesaid structural characteristics.

There continues to be a need for OLED materials exhibiting thermal stability, having bright, high purity luminescent emission, and for materials which contribute to greater luminescence per injected charge. There continues to be a need for OLED materials having color "tunability," which is the ability to modify the emissive output of a compound by attachment of substituent groups having absorptive or emissive characteristics.

SUMMARY OF THE INVENTION

In one aspect, the invention is a composition having visible-light-emissive, hole-transport, electron-transport, or bipolar-transport properties, and an organic light emitting device having such a composition in a functional layer thereof, comprising a non-polymeric compound with the following structure:

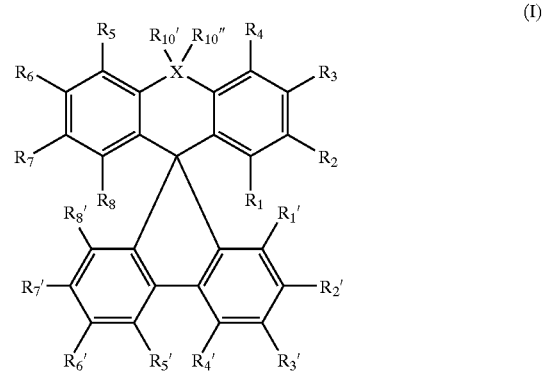

(I)

In the foregoing structure, X is a divalent, trivalent or tetravalent heteroatom. The fused ring structure incorporating heteroatom X is similar to anthracene, and the numbering of the substitutable carbon atoms $R_1$ through $R_8$ follows the numbering system conventionally used for anthracene. The fused ring structure containing substitutable carbon atoms $R_{1'}$ through $R_{8'}$ is a fluorene moiety and the numbering of these atoms follows the numbering system conventionally used for fluorene.

In the foregoing structure, $R_1$ through $R_8$, $R_{1'}$ through $R_{8'}$ and $R_{10'}$ and $R_{10''}$ independently represent a hydrogen atom, an alkyl group, an alicyclic group, an aralkyl group, an aryl group, an alkoxy group, an aryloxy group, a heterocyclic group, an amino group, an organometallic group or a nitro group. Any of the foregoing organic groups may be substituted or unsubstituted.

Of course, if X is divalent, X can not be substituted, and $R_{10'}$ and $R_{10''}$ are not present. If X is trivalent, only one of $R_{10'}$ and $R_{10''}$ may be present.

More particularly, where X is a divalent atom, such as sulfur or oxygen, there will not be substituent groups at X. An example is shown in FIG. (Ia), where the $R_3$ and $R_6$ positions are substituted with phenyl groups.

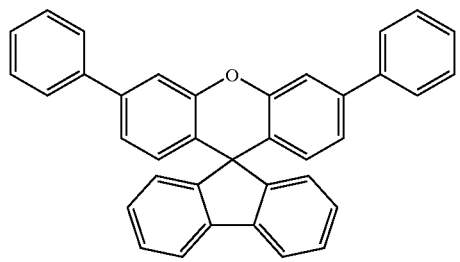

(Ia)

Where X is a trivalent atom, such a nitrogen, there can be only one substituent group at X. An example is shown in FIG. (Ib), wherein the 2 and 7 positions, and the nitrogen at the 10 position, are all substituted with phenyl.

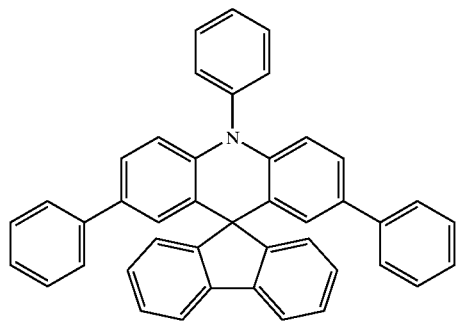

(Ib)

X may be tetravalent, but carbon is excluded. It is believed that substituting a heteroatom for carbon in the anthracene moiety imparts advantageous electronic properties for use of the subject compounds in OLEDs. An example where X is tetravalent silicon, and the silicon atom at the 10 position is substituted with two phenyl groups is shown in FIG. (Ic).

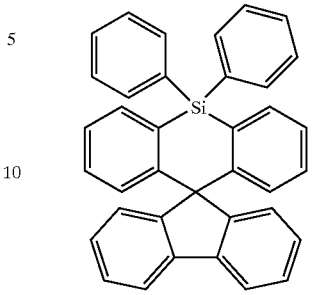

(Ic)

In another aspect, the invention is a composition capable of being used in an OLED in which two moieties having the structure of Formula I above are bonded to a common core. In this aspect, the invention is a composition having visible-light-emissive, hole-transport, electron-transport, or bipolar-transport properties in an OLED, comprising a non-polymeric compound represented by Formula II:

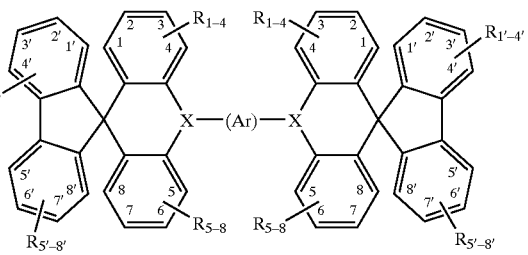

(II)

X is a trivalent atom, preferably nitrogen.

$R_{1-4}$, $R_{5-8}$, $R_{1'-4'}$ and $R_{5'-8'}$ are drawn intersecting the ring structures of Formula II. This means that one or more or all of the substitutable carbon atoms of each ring may be hydrogen atoms, alkyl groups, alicyclic groups, aralkyl groups, aryl groups, alkoxy groups, aryloxy groups, heterocyclic groups, amino groups, or organometallic groups, which groups may be substituted or unsubstituted, such that any of the substitutable carbon atoms in Formula II may be substituted with any of said groups.

In the foregoing Formula II, (Ar) may be alkyl, alkenyl, alkynyl, aryl, aralkyl or organometallic group, which may be substituted or unsubstituted. (Ar) is preferably a multi ring aromatic, such as biphenyl, which may be substituted or unsubstittued. (Ar) may also be a fused ring aromatic structures such as anthracene.

The invention is also directed to an OLED having a functional layer comprising one or more compositions described by Formula I or Formula II.

This brief summary has been provided so that the nature of the invention may be understood quickly. A more complete understanding of the invention can be obtained by reference to the following detailed description of the preferred embodiments thereof.

DETAILED DESCRIPTION OF THE PREFERRED EMBODIMENTS

In compounds according to Formula (I), X may be a divalent atom of oxygen or sulfur. If X is oxygen, Formula (I) comprises a xanthene moiety and a fluorene moiety linked by a common spiro carbon atom, as shown below:

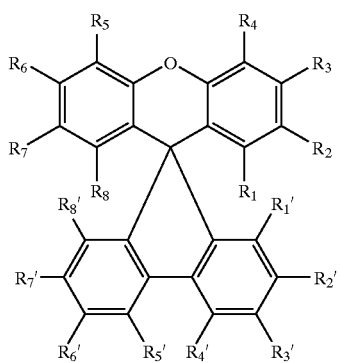

(I')

The compound Spiro-9-fluorene-9'-xanthene may be synthesized, for example, by starting from fluorenone and a Grignard reagent prepared from a functionalized diphenyl ether according to the method disclosed in U.S. Pat. No. 5,763,636, incorporated herein by reference.

According to the aforesaid U.S. Pat. No. 5,763,636, Spiro 9-fluorene-9'-xanthene must be polymerized to obtain a polymer having emissive characteristics useful in an OLED. According to the present invention, compounds having electronic properties suitable for use in an OLED may also be obtained in a non-polymeric ("small") molecule. For example, if the $R_3$ and $R_6$ positions of the anthracene moiety of spiro 9-fluorene-9'-xanthene are occupied with phenyl groups as in Formula (Ia),

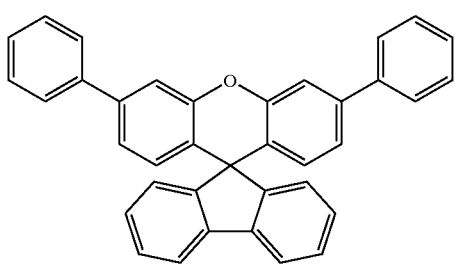

(Ia)

the resulting compound is expected to be emissive, and can be used in an OLED using vacuum deposition techniques.

In general, any of $R_1$–$R_8$ or $R_1'$–$R_8'$ may be hydrogen. In general, at least one substitution must be made to the compound to impart emissive or charge transport characteristics.

Any of $R_1$–$R_8$ or $R_1'$–$R_8'$ may be substituted or unsubstituted alkyl, substituted or unsubstituted alicyclic, substituted or unsubstituted aralkyl group, a substituted or unsubstituted aryl group, a substituted or unsubstituted alkoxy or aryloxy group, a substituted or unsubstituted heterocyclic group, an amino group, an organometallic group or a nitro group.

Alkyl group means straight and branched chain alkyl groups and non-limiting examples include methyl, ethyl and tert-butyl. Substituted, in this context, means that one or more of the hydrogen atoms of the alkyl group is substituted with another functional group, such as without limitation, halogen. Thus chloromethyl is a non-limiting example of a substituted alkyl group.

Aryl group means any aromatic ring structure, including multi-ring structures, such as without limitation, phenyl, biphenyl or terphenyl. Aryl also includes fused ring structures, such as without limitation, anthracene, phenanthracene, perylene and the like. Substituted in this context includes the same substitutions given above for alkyl, but also includes substitution of one or more of the hydrogen atoms of the aryl group with an alkyl group. Thus, a non-limiting example of a substituted aryl is a toluyl group.

Aralkyl means a group including at least one alkyl moiety bonded to at least one aryl moiety, bonded to the base compound at the alkyl moiety. Aryloxy and alkoxy refer to compounds in which an aryl or alkyl group is bonded to an oxygen which is bonded to the base compound, as in alkoxy or benzoxy.

Heterocyclic means an aryl or alicyclic group in which one of the carbons of the ring is substituted with a heteroatom such as without limitation sulfur, oxygen, or nitrogen. Heterocyclic includes multi-ring structures having heteroatoms.

Compounds according to Formula (Ia) may be made starting with a Grignard reagent prepared from a halogen functionalized di-biphenyl ether compound and magnesium, adding fluorenone and reacting under refluxing conditions according to the method outlined in U.S. Pat. No. 5,763,636. Alternatively, starting with 9-fluorene-9'-xanthene, appropriate substitutions could be performed using known techniques such as those methods outlined in Tour, et al., *J. Org. Chem.*, 1996, 61(6906–6921).

In another embodiment, the invention is directed to compounds having emissive or charge transport characteristics, which have a structure according to Formula (I) above wherein X is nitrogen. The resulting compounds comprise an acridine moiety bonded to a fluorene moiety by a common spiro atom at the 9, 9' position.

Starting with fluorenone, as in the previous example, and a halogen functionalized arylamine, a compound having the structure of Formula (III) can be prepared:

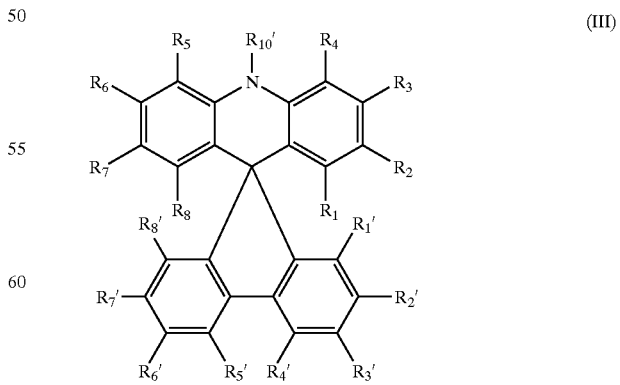

(III)

A particularly preferred embodiment has the structure of Formula (Ib) above, based on triarylamine. Based on the excellent hole transporting properties of many of the aromatic amines, and based further on the excellent stabilizing properties of the fluorene moiety as a host, the subject compound is expected to exhibit novel properties in an OLED.

In still another embodiment, compounds according to the invention have a tetraphenylsilane moiety and a fluorene moiety linked by a common spiro carbon atom, as shown in Formula (IV):

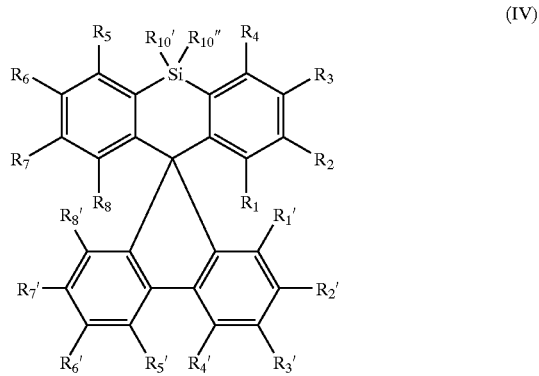

The above compound can be made by reacting an appropriately functionalized silane compound with a fluorenone. Suitable starting silane compounds may be prepared according to methods set forth in U.S. Pat. No. 5,859,211, incorporated herein by reference.

Where X is trivalent nitrogen, multiple groups of Formula (III) may be attached to a single organic core as shown below in Formula (IIa). The resulting compounds have hole transport capability:

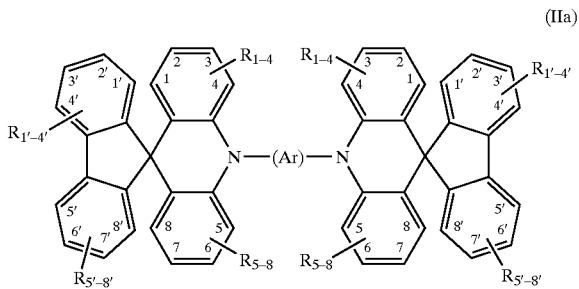

The above structure (IIa) can be synthesized starting with a spiro 9-fluorene-9'-acridine moiety, which may bear substituent groups. This starting material is reacted with an "Ar" group which has been di-functionalized with halogen. The reaction is performed by refluxing the starting materials in the presence of metal and base, substantially in accordance with co-pending application Ser. No. 10/029,936. Thus, for example, if Ar is to be biphenyl, one equivalent of diiodobiphenyl is reacted with two equivalents of the 9-fluorene-9'-acridine in the presence of copper powder, and potassium carbonate in a Crown-6 ether solution. The resulting mixture is refluxed under nitrogen with 1,2-dichlorobenzene and the product purified.

Those of ordinary skill in the art will recognize that (Ar) in Formulas (II) and (II a) is divalent. However, (Ar) could easily be made trivalent or tetravalent, and a corresponding number of groups according to Formula (III) attached.

To form an OLED an anode material with a high work function is deposited on a transparent substrate. Preferably ITO is used as the anode material, but other suitably high work function materials (greater than about 4 eV) are known in the art. The anode is preferably vacuum deposited to a thickness of 10 nm to 1000 nm, more preferably to a thickness of about 10 nm to about 100 nm.

Glass or quartz is the preferred substrate, but transparent polymeric materials known to those of ordinary skill in the art may also be used, including without limitation, polycarbonates, polymethacrylates, and polyether sulfones.

A blocking layer to retain charge in the functional layers may be deposited adjacent the anode as sometimes practiced in the art. A blocking layer restricts the diffusion of electrons toward the anode. A modifying layer, also sometimes called a hole injection layer may optionally be deposited adjacent the anode to facilitate the charge transport from the anode into the hole transport layer, directly into the emissive layer, or into the hole transport/emissive layer.

Optionally, a hole transporting layer is deposited to a thickness of about 5 nm to about 1000 nm, preferably about 10 to about 500 nm. A hole transporting layer according to the invention may be used, such as a compound according to Formula (II a) above, wherein (Ar) is biphenyl. Others of the hole transporting compounds disclosed in the prior art may be used. Suitable hole transport materials include amine compounds CPB, TBD, NPD, and the like. Other suitable materials are disclosed in U.S. Pat. Nos. 5,698,740, 5,942,340, and U.S. patent application Publication 2002/0045062, herein incorporated by reference for their disclosure of known materials useful in OLEDs.

An emissive layer is deposited between the anode and the cathode, preferably directly on the hole transport layer. A hole transport material may be combined with an emissive material. For example, a compound according to Formula (II) in which (Ar) is an emissive group comprising fused aromatic rings (anthracene, perylene, phenanthracene and the like) may be added to the emissive layer. Likewise, compounds according to FIG. (I), in which X is Si or O, may be added to the emissive layer. Numerous emissive materials have been disclosed in the art, including the above-mentioned fused aromatic ring structures, organic metal complexes and others. The emissive layer is preferably vacuum deposited to a thickness of about 10 nm to about 1000 nm, preferably about 10 nm to about 500 nm.

An electron transport material, such as without limitation, the above mentioned AlQ3 material, may be deposited to a thickness of about 10 nm to about 1000 nm, preferably about 10 nm to about 500 nm. Other suitable electron transport materials are disclosed in the aforesaid U.S. Pat. Nos. 5,698,740, 5,942,340, and U.S. patent application Publication 2002/0045062. Optional blocking layers and/or contact modifying layers may be provided adjacent the cathode.

Finally a low work function cathode is deposited such as Al, Ca or Mg to a thickness of about 10 nm to 1000 nm, more preferably to a thickness of about 10 run to about 100 nm.

EXAMPLES

An anode material of ITO is vapor deposited on a glass substrate at in a vacuum of about $5 \times 10^{-6}$ Torr. A hole transport compound according to Formula (Ib) is deposited under the same conditions to a thickness of 50 nm. Emissive aluminum quinolinolate complex (AlQ3) is deposited under the same conditions to about the same thickness. Finally, an Al cathode layer is deposited, also having about the same thickness. The completed OLED produces visible emission upon an application of a driving voltage less than 20 V.

An OLED is manufactured as set forth in the preceding paragraph except that for the emissive layer, in place of the layer of AlQ3, is deposited to about the same thickness a guest-host layer having 5 percent by weight of emissive tris (2-phenylpyridine) iridium (Ir(ppy3)) guest compound doped into a host composition according to Formula II, wherein (Ar) is biphenyl and X is nitrogen. The completed modified OLED produces visible emission upon an application of a driving voltage less than 20 V.

Broadly, devices according to the invention have a driving voltage between 1 V and 100 V. However, in most useful displays, it is preferable to obtain a device having a driving voltage of less than about 20 V. While it is always desirable to achieve brighter emission, a practical device typically exhibits a maximum brightness of at least about 100 cd/m$^2$, preferably greater.

It is preferred to deposit the non-polymeric materials of the invention by vacuum deposition. Other dry film forming processes such as ion plating, molecular beam epitaxial growth may also be used. The disclosed compounds can also be dissolved in a solvent and deposited using solution-based techniques.

What is claimed is:

1. A non-polymeric compound having visible-light-emissive, hole-transport, electron-transport, or bipolar-transport properties, having the following structure:

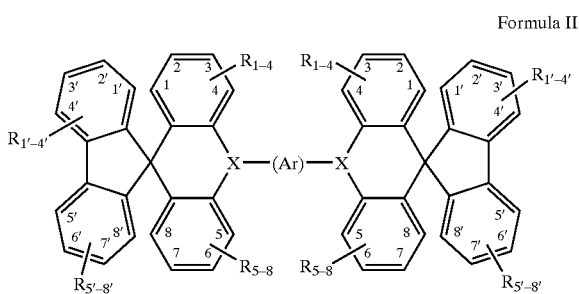

Formula II wherein X is a trivalent atom, wherein $R_{1-4}$, $R_{5-8}$, $R_{1'-4'}$ and $R_{5'-8'}$ independently represent hydrogen atoms, alkyl groups, alicyclic groups, aralkyl groups, aryl groups, alkoxy groups, aryloxy groups, heterocyclic groups, amino groups, or organometallic groups, which groups may be substituted or unsubstituted, such that any of the substitutable carbon atoms in Formula II may be substituted with any of said groups, and wherein (Ar) is an alkyl, alkenyl, alkynyl, aryl, aralkyl or organometallic group, which may be substituted or unsubstituted.

2. A compound according to claim 1, wherein X is nitrogen and the compound has hole transport capability.

3. A compound according to claim 1, wherein X is nitrogen and (Ar) is multi-ring aromatic.

4. A compound according to claim 1, wherein X is nitrogen and (Ar) is biphenyl.

5. An organic light emitting device comprising an anode, a cathode and functional layers, having at least one functional layer comprising a compound according to claim 1.

6. An organic light emitting device according to claim 5, wherein said functional layer is a charge transport layer.

7. An organic light emitting device according to claim 5, wherein said functional layer is a bipolar charge transport layer.

8. An organic light emitting device according to claim 5, wherein said functional layer has a fluorescent or phosphorescent emission in the visible range.

9. An organic light emitting device according to claim 5, wherein said functional layer is a guest-host system, and the compound according to claim 1 is a host in said system.

* * * * *

UNITED STATES PATENT AND TRADEMARK OFFICE
CERTIFICATE OF CORRECTION

PATENT NO. : 7,014,925 B2 Page 1 of 1
APPLICATION NO. : 10/424743
DATED : March 21, 2006
INVENTOR(S) : Travis P.S. Thoms It is certified that error appears in the above-identified patent and that said Letters Patent is hereby corrected as shown below:

COLUMN 8
Line 56, "10 run" should read --10 nm--.

Signed and Sealed this

Seventh Day of November, 2006

JON W. DUDAS
*Director of the United States Patent and Trademark Office*